US012588854B2

(12) United States Patent (10) Patent No.: US 12,588,854 B2
Botzer et al. (45) Date of Patent: Mar. 31, 2026

(54) ALGORITHM FOR OPTIMAL BEAT SELECTION

(71) Applicant: Biosense Webster (Israel) Ltd., Yokneam (IL)

(72) Inventors: Lior Botzer, Timrat (IL); Meir Bar-Tal, Haifa (IL); Guy David Malki, Petah Tikva (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 455 days.

(21) Appl. No.: 17/985,216

(22) Filed: Nov. 11, 2022

(65) Prior Publication Data

US 2023/0157615 A1 May 25, 2023

Related U.S. Application Data

(60) Provisional application No. 63/281,963, filed on Nov. 22, 2021.

(51) Int. Cl.
*A61B 5/347* (2021.01)
*A61B 5/349* (2021.01)
*A61B 5/367* (2021.01)

(52) U.S. Cl.
CPC .............. *A61B 5/347* (2021.01); *A61B 5/349* (2021.01); *A61B 5/367* (2021.01)

(58) Field of Classification Search
CPC .......... A61B 5/347; A61B 5/349; A61B 5/367
USPC ....................................................... 600/509
See application file for complete search history.

(56) References Cited

U.S. PATENT DOCUMENTS

| | | | |
|---|---|---|---|
| 6,814,733 B2 | 11/2004 | Schwartz et al. | |
| 6,961,602 B2 | 11/2005 | Fuimaono et al. | |
| 6,997,924 B2 | 2/2006 | Schwartz et al. | |
| 7,156,816 B2 | 1/2007 | Schwartz et al. | |
| 7,536,218 B2 | 5/2009 | Govari et al. | |
| 7,756,576 B2 | 7/2010 | Levin | |
| 8,137,343 B2 * | 3/2012 | Harlev | A61B 5/0536 |
| | | | 600/509 |
| 8,456,182 B2 | 6/2013 | Bar-tal et al. | |
| 9,023,027 B2 | 5/2015 | Bar-tal et al. | |
| 9,380,953 B2 | 7/2016 | Houben et al. | |
| 9,414,770 B2 | 8/2016 | Bar-tal et al. | |
| 2007/0299352 A1 | 12/2007 | Harlev et al. | |
| 2008/0249424 A1 | 10/2008 | Harlev et al. | |

(Continued)

OTHER PUBLICATIONS

Communication pursuant to Article 94(3) EPC dated Jun. 3, 2025 for European Patent Application No. 22 817 357.1.

(Continued)

*Primary Examiner* — Nadia A Mahmood
(74) *Attorney, Agent, or Firm* — Volpe Koenig

(57) ABSTRACT

Systems and methods for optimal selection of beats for a 3D mapping are disclosed. A method in accordance with the present disclosure may be performed on a processor and may comprise receiving a plurality of beats from a catheter. The catheter may be located at a target mapping site, such as a chamber of the heart. A plurality of dynamic filters may be applied to the plurality of collected beats. The optimal beats may be determined and integrated as a beat in the 3D mapping system. This method enables the selection of more beats for a more comprehensive 3D mapping, as well as the selection of more quality beats that are representative of the target anatomy.

20 Claims, 9 Drawing Sheets

(56)     References Cited

U.S. PATENT DOCUMENTS

| | | | |
|---|---|---|---|
| 2012/0184858 | A1 | 7/2012 | Harlev et al. |
| 2012/0184865 | A1 | 7/2012 | Harlev et al. |
| 2015/0164356 | A1 | 6/2015 | Merschon et al. |
| 2015/0289807 | A1 | 10/2015 | Narayan et al. |
| 2017/0189134 | A1 | 7/2017 | Chmiel et al. |
| 2018/0008203 | A1 | 1/2018 | Iyun et al. |
| 2018/0042504 | A1 | 2/2018 | Botzer et al. |
| 2021/0038171 | A1 | 2/2021 | Katz et al. |
| 2021/0196372 | A1 | 7/2021 | Altmann et al. |

OTHER PUBLICATIONS

International Search Report mailed Jan. 30, 2023 for PCT International Application No. PCT/IB2022/061027.
Written Opinion of the International Searching Authority dated May 25, 2023 for PCT International Application No. PCT/IB2022/061027.

\* cited by examiner

810

811

820

821

ALGORITHM FOR OPTIMAL BEAT SELECTION

CROSS REFERENCE TO RELATED APPLICATIONS

This application claims the benefit of 63/287,963 filed Nov. 22, 2021, which is incorporated by reference as if fully set forth.

FIELD OF INVENTION

This disclosure relates to constructing a model of an internal volume. More particularly, this disclosure relates to constructing a three-dimensional (3D) model of an anatomical structure.

BACKGROUND

Medical applications may call for constructing a model of an anatomical structure, such as a chamber of a heart. In current implementations, a catheter may be moved within the chamber of the heart and the location of the catheter may be continually recorded by a tracking system. The collected beats may be integrated into a 3D mapping which may represent the chamber of the heart. The 3D mapping may be a 3D electro-anatomical map comprising hundreds, thousands, or tens of thousands of electro-anatomical beats, along with gaps in which no beats are present.

Electrocardiograms (ECGs) and electrograms (EGMs) may be used to generate a mapping. ECGs are generated from electrical signals from a heart that describe heart activity. ECGs are utilized during cardiac procedures to identify potential origination locations of cardiac conditions. ECGs signals may also be used to map portions of a heart. EGMs may be recorded from each of the electrodes in contact with a cardiac surface relative to a temporal reference such as the onset of a P-wave in sinus rhythm from a body surface ECG. ECG and EGM signals may be utilized with rule-based algorithms to determine cardiac mapping annotations, such as that described in U.S. Patent Publication No. US2018/0042504.

Current systems acquire and record a first signal or "beat" at every spatial location, even if the beat has poor characteristics. However, it would be desirable to detect and select the best beat at each spatial location as a mapping annotation. Further, once a beat is collected, it is automatically integrated into the mapping and cannot be removed. It would be desirable to dynamically filter beats such that if a better beat is collected, the better beat may be integrated into the mapping and the inferior beat may be removed.

SUMMARY

Systems and methods for optimal selection of beats for a 3D mapping are disclosed. A method in accordance with the present disclosure may be performed on a processor and may comprise receiving a plurality of beats from a catheter. The catheter may be located at a target mapping site, such as a chamber of a heart. A plurality of dynamic filters may be applied to the plurality of collected beats. The optimal beats may be determined and integrated as a beat in a 3D mapping system. This method enables the selection of more beats for a more comprehensive 3D mapping, as well as the selection of more quality beats that are representative of the target anatomy.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1:
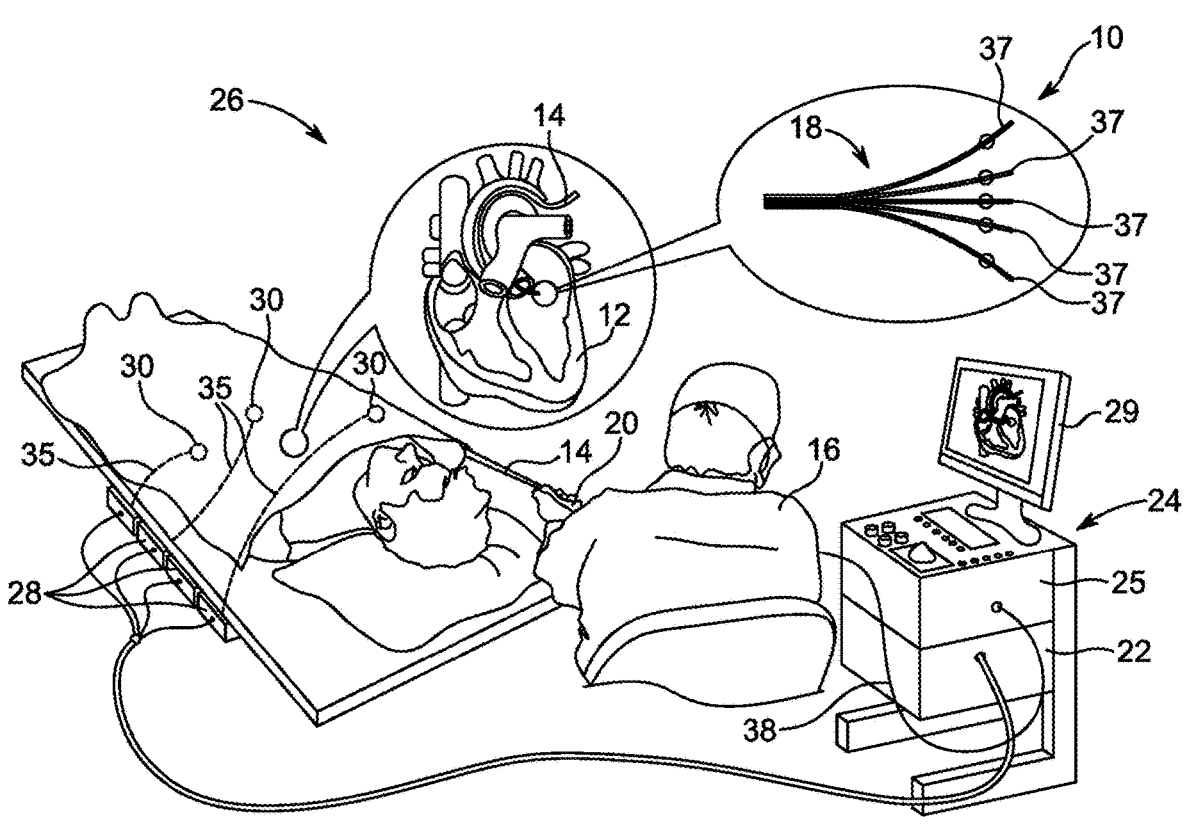
FIG. 1 is a schematic, pictorial illustration of a system for performing procedures on a heart of a living subject using a cardiac catheter having multiple branches, according to an exemplary embodiment.

FIG. 1 is a schematic, pictorial illustration of a system 10 for performing procedures on a heart 12 of a living subject, according to an embodiment. The system 10 may comprise a catheter 14 and a control console 24. One commercial product embodying elements of the system 10 is available as the CARTO® 3 System, available from Biosense Webster, Inc.

The catheter 14 may be used for any suitable therapeutic and/or diagnostic purposes, such as anatomical mapping of a cavity in a heart 12. The catheter 14 may be a multi-electrode catheter having an elongated body with multiple branches 37, each having mapping and location sensing capabilities. The catheter 14 may further comprise a handle 20, having controls which enable an operator 16, who is typically a physician, to steer, position and orient the distal end of the catheter 14 and the location and orientation of the branches 37 as necessary. In one example, the catheter described in commonly assigned U.S. Pat. No. 6,961,602, having five branches, is suitable for use as the catheter 14. This catheter is available as the Pentaray™ catheter or probe from Biosense Webster. Any number of other mapping/diagnostic catheter types may be used in other examples, including lasso-type, basket-type, or grid-type catheters, such as the OCTARAY™, LASSO™, and OPTRELL™ catheters, also from Biosense Webster.

In some embodiments, the catheter 14 comprises an elongated body having a proximal end, a distal end, and at least one lumen extending longitudinally therethrough, and a mapping assembly mounted at the distal end of the catheter body and comprising at least two branches 37. Each branch 37 has a proximal end attached at the distal end of the catheter body and a free distal end. Each branch 37 comprises a support arm having shape memory, a non-conductive covering in surrounding relation to the support arm, at least one location sensor (FIG. 2) mounted in the distal end of the branch 37, one or more electrodes mounted on the distal end of the branch 37 and electrically isolated from the support arm, and one or more electrode lead wires extending within the non-conductive covering, each electrode wire being attached to a corresponding electrode. In some embodiments, additional location sensors (not shown) may be disposed on the shaft of the catheter 14 proximal to the branches 37.

The catheter 14 may be percutaneously inserted by the operator 16 through the patient's vascular system into a chamber or vascular structure of the heart 12. The operator 16 may bring the catheter's distal tip 18 in contact with the heart wall at a desired mapping site. The distal end of the catheter 18 may then collect measurement signals, or "beats."

Ablation energy and electrical signals may be conveyed to and from the heart 12 through one or more optional ablation electrodes located at or near the distal tip of a catheter configured to ablate tissue through a cable to the console 24. Pacing signals and other control signals may be conveyed from the console 24 through the cable 38 and the one or more ablation electrodes to the heart 12.

Wire connections 35 may link the console 24 with body surface electrodes 30 and other components of a positioning sub-system. A temperature sensor 43 (FIG. 2), such as a thermocouple or thermistor, may be mounted on or near the distal tip 18.

The console 24 may comprise one or more ablation power generators 25. A catheter, in some cases a separate catheter not shown, may be configured to conduct ablative energy to the heart using any known ablation technique, including but not limited to, radiofrequency energy, pulsed-field ablation "PFA" (sometimes referred to as irreversible electroporation or "IRE"), ultrasound energy, and laser-produced light energy. Such methods are disclosed in commonly assigned U.S. Pat. Nos. 6,814,733, 6,997,924, and 7,156,816, and U.S. Patent Publication No. US20210196372A1, which are herein incorporated by reference as is fully set forth.

The processor 22 may be an element of a positioning system 26 of the system 10 that measures location and orientation coordinates of the catheter 14.

In some embodiments, the positioning system 26 may comprise a magnetic position tracking arrangement that determines the position and orientation of the catheter 14 by generating magnetic fields in a predefined working volume in its vicinity and sensing these fields at the catheter 14 using field generating coils 28 and may include impedance measurements, as taught, for example in commonly assigned U.S. Pat. No. 7,756,576, which is herein incorporated by reference as if fully set forth. The positioning system 26 may be enhanced by position measurements using the impedance measurements described in commonly assigned U.S. Pat. No. 7,536,218, which is herein incorporated by reference as if fully set forth.

As noted above, the catheter 14 is coupled to the console 24, which enables the operator 16 to observe and regulate the functions of the catheter 14. Console 24 includes a processor 22. The processor 22 may be coupled to a display 29. The signal processing circuits may receive, amplify, filter, and digitize signals from the catheter 14, including signals generated by the above-noted sensors and a plurality of location sensing electrodes (not shown) located on the catheter 14. The digitized signals may be received and used by the console 24 and the positioning system 26 to compute the position and orientation of the catheter 14 and to analyze the electrical signals from the electrodes. As used herein, a "beat" may refer to a signal measured by the catheter 14.

In some embodiments, the processor 22 may be a computer, and may be programmed in software to carry out the functions described herein. For example, in some embodiments, the processor 22 is a programmed digital computing device comprising a central processing unit (CPU), a graphics processing unit (GPU), a random access memory (RAM), non-volatile secondary storage, such as a hard drive or CD ROM drive, network interfaces, and/or peripheral devices. Program code, including software programs, and/or data are loaded into the RAM for execution and processing by the CPU and/or GPU, and results are generated for display, output, transmittal, or storage, as is known in the art. The software code may be downloaded to the computer in electronic form over a network, or it may be provided and/or stored on non-transitory tangible media, such as magnetic, optical or electronic memory.

Figure 2:
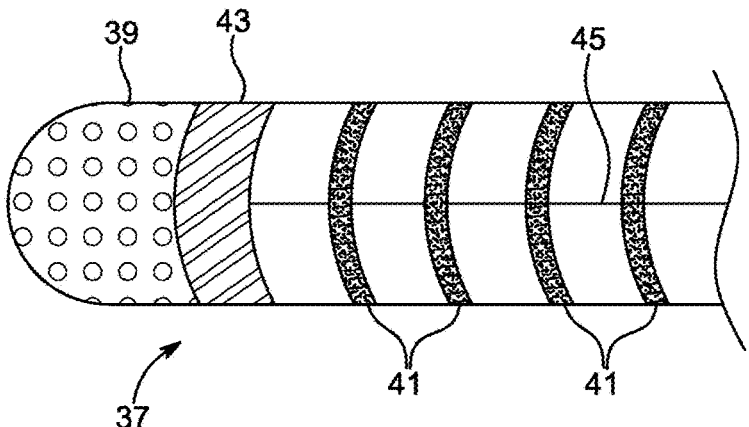
FIG. 2 is a is a detailed view of one of the branches of the catheter shown in FIG. 1, according to an exemplary embodiment.

FIG. 2 is a detailed view of one of the branches 37 of FIG. 1, showing an electrode configuration, according to an embodiment. The electrode configuration may comprise a tip electrode 39, two ring electrodes 41, and a temperature sensor 43. In other examples, in addition to sensing, tip electrode 39 may be additionally configured for ablation. In such examples, temperature sensor 43 may be used when the catheter 14 is in an ablation mode. The two ring electrodes 41 may be configured as sensing electrodes to detect electrophysiologic signals in the heart. However, as will be appreciated by one having ordinary skill in the art, the sensing electrodes and ablation electrodes may vary in number, configuration, and distribution in many combinations. One or more cables 45 may communicate signals between the electrodes, sensors, and the console 24. With multiple electrodes distributed in several branches 37, it is possible to collect signals from many locations simultaneously.

In the catheter 14 illustrated in FIGS. 1 and 2, multiple electrodes may be positioned on different spines. The distribution of spines when in contact with the tissue may vary in different sessions, or even in the same session as the catheter 14 is manipulated by the operator. As a result, the distances between electrodes on different spines may vary, and generally are not uniform during the signal collection process.

Medical applications may call for constructing a model of an anatomical structure, such as a chamber of a heart. In current implementations, a catheter may be moved within the chamber of the heart in order to collect electro-anatomical signals or "beats". The catheter may be a multielectrode catheter, such as the Pentaray™ catheter or probe from Biosense Webster. The collected beats may be selected to be a point in a 3D mapping, sometimes referred to as an electroanatomical map or simply a map, which represents the anatomy of and electrical signals propagating in a chamber of the heart. As used herein, the term "point" is defined as a beat with an associated location. The 3D mapping may include hundreds, thousands, or tens of thousands of beats, along with gaps in which no beats are present.

Current mapping implementations are optimized for quick data collection. For example, in current implementations, the first beat that meets some predefined criteria is collected automatically and incorporated into the map. Other beats in the same region are not selected, regardless of whether the selected beat has higher noise levels, contains far field, or is not in agreement with other adjacent beats. Additionally, the selection of beats is not dynamic, such that once they are collected and selected, they cannot be removed. Further, current implementations are memoryless, such that only selected beats are retained, while all other data is ignored.

In view of the foregoing, improved systems directed at optimal beat selection would be beneficial. A system for dynamically selecting optimal beats for integration into a mapping, without saturating the mapping with redundant data, is disclosed. The disclosed system and methods may collect more beats which may then be dynamically filtered. As such, not only more beats may be selected for a more comprehensive mapping, the selected beats are better quality and more representative of the target anatomy.

A system in accordance with the present disclosure may comprise a processor 22 and a memory, as described above. The memory may comprise instructions, which, when executed, cause the processor 22 to apply an algorithm to collected beats such that optimal beats are selected for integration into a mapping. As such, only the most valuable beats may be selected.

Figure 3:
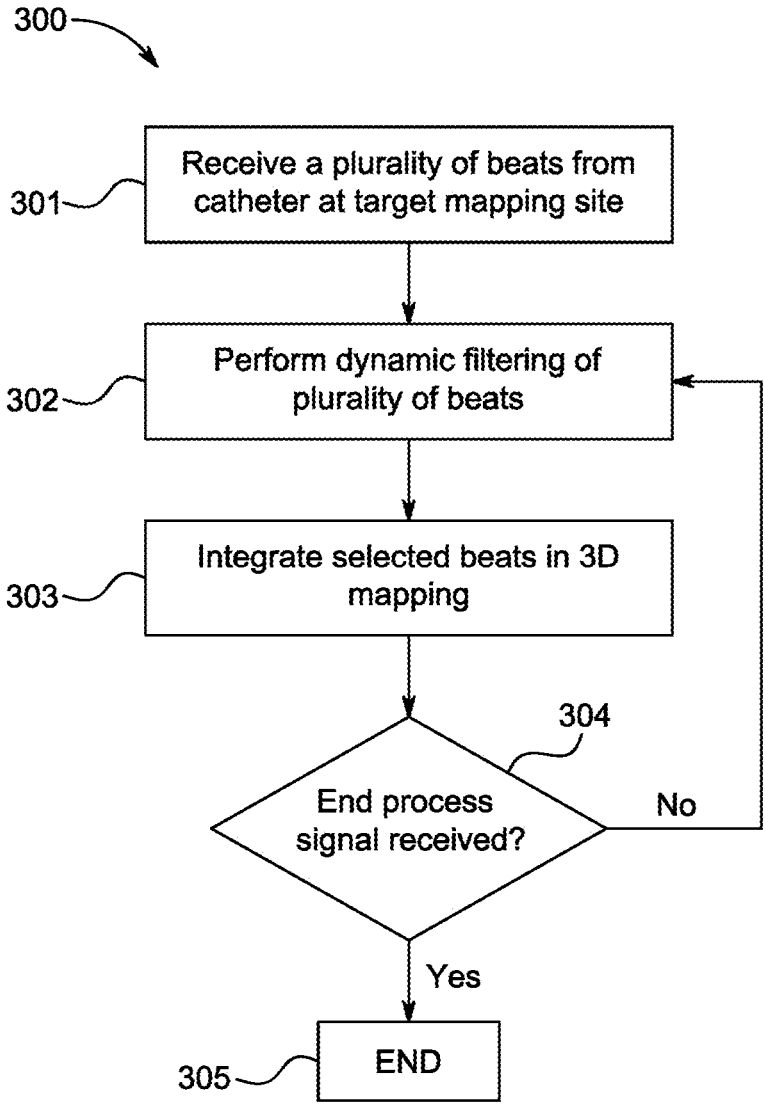
FIG. 3 is a flow chart of a method for optimal beat selection for a 3D anatomical reconstruction, according to an exemplary embodiment.

FIG. 3 is a flow chart of a method 300 for optimal beat selection for a 3D anatomical reconstruction, according to an exemplary embodiment. At 301, the processor 22 may acquire a plurality of beats. The plurality of beats may be taken by a catheter, such as the catheter 14 described above with respect to FIGS. 1 and 2. The operator 16 may bring the catheter's distal tip 18 in contact with the heart wall at a desired target mapping site to acquire the plurality of beats. In some embodiments, as many beats as possible are collected. At 302, the processor 22 may apply an algorithm for optimal beat selection. The algorithm may provide dynamic filtering of the beats to determine which beats are selected for the 3D mapping of the desired anatomical structure. In some embodiments the algorithm may be comprised of multiple phases. For example, in some embodiments, the algorithm may comprise three phases: Phase I, Phase II, and Phase III. The algorithm for dynamically filtering the beats is described in more detail below. In some embodiments, the desired anatomical structure is a chamber of the heart. At 303, if a beat if selected, it is integrated into the 3D mapping which represents the desired anatomical structure. At 304 it is determined whether an end process signal has been received. If an end process signal has not been received, the method returns to step 302, and the algorithm continues to dynamically filter the collected beats. If an end process signal has been received, the method ends at 305.

The algorithm for dynamically filtering the collected beats is now discussed in more detail. In some embodiments, the algorithm applies a plurality of filters. In some embodiments, the plurality of filters comprise one or more of:

position stability, spatial density, inner distance, catheter filter, cycle length, cycle length stability, ventricle activity blanking, respiration, pattern matching, local activation time (LAT), LAT stability, unipolar slope, bipolar voltage, tissue proximity indicator (TPI) or value, presence of special signals with special clinical features such as fractionation with and or without stability indication, and noise level. However, this list is not exhaustive and other filters may be utilized.

The algorithm may comprise a position stability filter, as noted above. In some embodiments, position stability is used in a Phase I of the algorithm. In some embodiments, the processor 22 may measure changes in the location of the catheter 14 during the collection of beats. In further embodiments, the processor 22 may account for respiratory movement when measuring changes in the location of the catheter 14. The position stability may refer to the measurement of changes in the location of the catheter 14 during the collection of beats. In some embodiments, the position stability filter may require that the variation of the location of the catheter 14 over a defined time window be not greater than a predefined maximum distance. The variation may be measured in terms of standard deviation about the mean position during the defined time window. The position may be corrected/estimated to its "true" location relative to the heart structures while eliminating artificial movements arising from respiration.

The algorithm may comprise a spatial density filter, as noted above. In order to avoid selecting multiple beats with similar characteristics and adding them to the 3D mapping, the spatial density filter is used. In some embodiments, the spatial density filter may divide the 3D mapping space into voxels. As used herein, the term "voxel" is defined as a discrete element of a regularly spaced, 3D dimensional grid. In some embodiments, the voxels are one mm$^3$ in size. In some embodiments, the location of the electrode may be recorded when the ECG activity was detected and all of the beats collected in a single voxel may be determined. The spatial density filter may choose only one of the beats according to a predefined criteria.

The algorithm may comprise an inner distance filter, as noted above. In some embodiments, the location of the electrode may be recorded when the ECG activity was detected. The inner distance may be defined as the distance from the outer surface of the 3D mapping to where points are trajected onto the map. In some embodiments, beats with a minimal inner distance may be favored to reduce error.

The algorithm may comprise a catheter filter, as noted above. In some embodiments, multiple catheters may be utilized to collect beats. In these embodiments, the catheter filter may be used to select beats collected from one or more particular catheters.

The algorithm may comprise a cycle length filter, as noted above. In some embodiments, only beats with a certain cycle length range may be considered for selection. Cycle length is a measure which aids in the determination of whether a beat has the same tachycardia as other beats. Normally, beats are collected as long as their cycle length is within a predefined range, based on the existing tachycardia type and duration. For example, the predefined range may be about 300 ms to about 330 ms. However, this predefined range is by way of example only, and other predefined ranges may be used.

Figure 4:
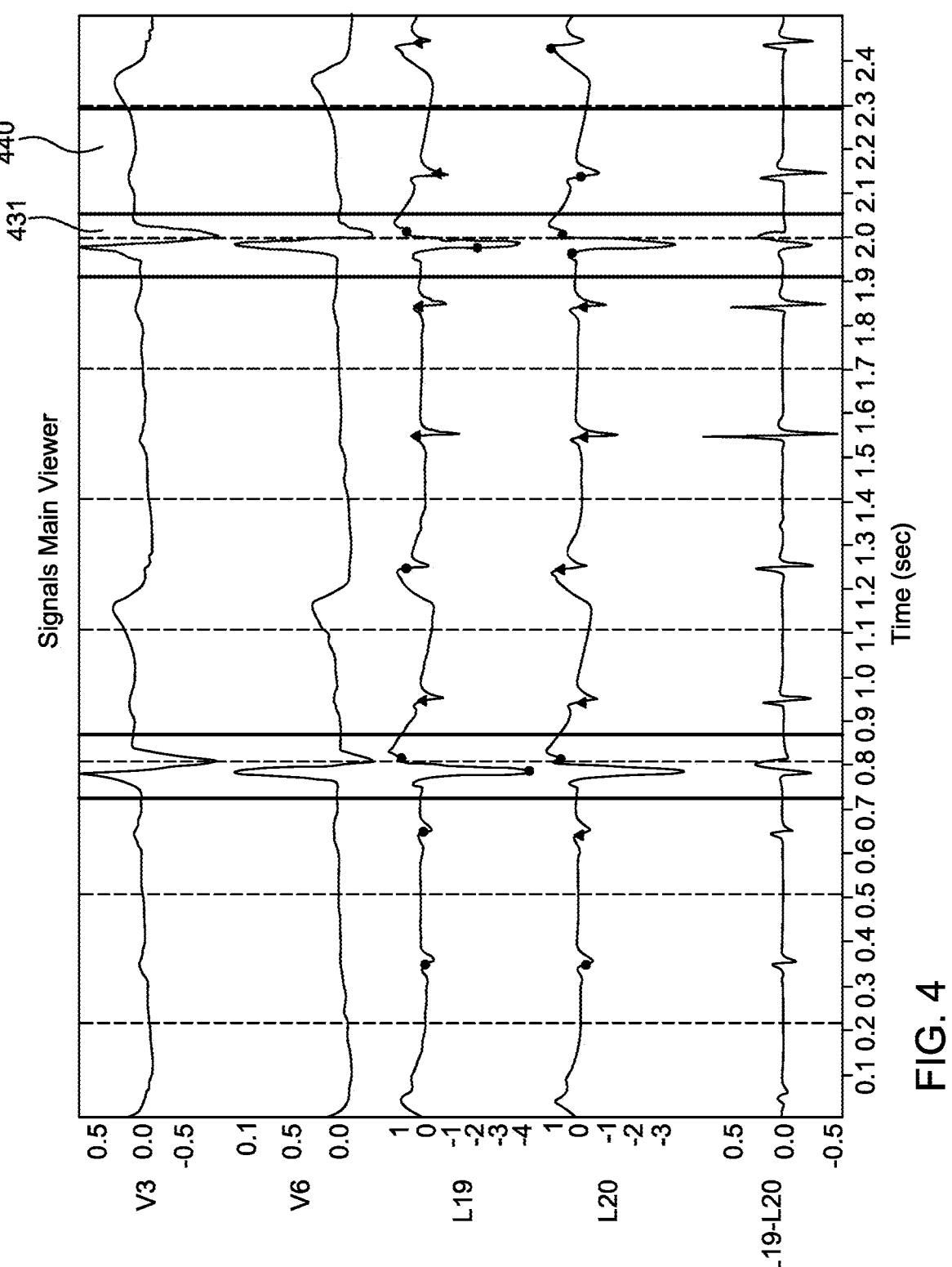
FIG. 4 is a graph of electrode activity illustrating a ventricle activity blanking filter, according to an embodiment.

The algorithm may comprise a ventricle activity blanking filter, as noted above. In some embodiments, one or more areas of ventricular activity 440 may be determined, as shown in FIG. 4. If these one or more areas of ventricular activity 440 overlap with a beat of interest, such as beat 431, the beat may not meet the ventricle activity blanking filter, and therefore the beat may be discarded. Further, when a heart ventricle contracts, the ventricle activity may be observed as a far-field signal. Additionally, or alternatively, to the one or more areas of ventricular activity being determined, a far field component of a signal may be determined. If a beat is located on the far field component of the signal, the beat may not meet the ventricle activity blanking filter, and the beat may be discarded.

The algorithm may comprise a respiration filter, as noted above. A respiration cycle indication may be a value indicating at which time a measurement is in the respiration cycle. In some embodiments, the algorithm may only incorporate beats collected at the end of expiration. This would minimize or eliminate the affect that respiration has on the mapping, thereby reducing error in the mapping. The respiration cycle indication may be determined using systems and methods disclosed in commonly assigned U.S. Pat. Nos. 8,456,182, 9,414,770 and 9,023,027, which are incorporated by reference as if fully set forth.

The algorithm may comprise a pattern matching filter, as noted above. The pattern matching filter may determine whether two beats come from the same tachycardia. In some embodiments, this is determined using a reference catheter, such as a coronary sinus catheter, as described in commonly assigned U.S. Pat. Nos. 8,456,182, 9,414,770 and 9,023,027, which are incorporated by reference as if fully set forth.

Figure 5:
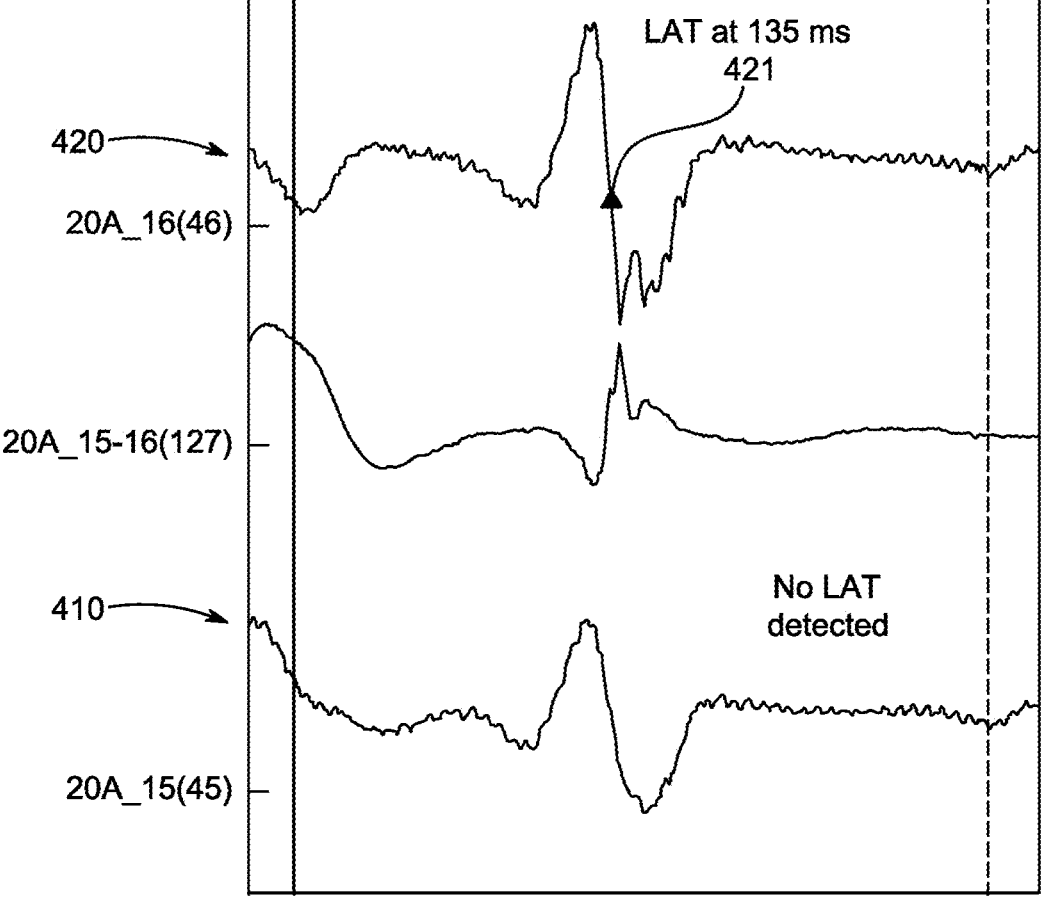
FIG. 5 is a graph of electrical activity with a beat for which LAT is not detected and a beat for which LAT is detected, according to an exemplary embodiment.

The algorithm may comprise a LAT filter, as noted above. The LAT of the electrical activity of at a desired location may be defined in terms of the electrical activity satisfying a predefined condition. FIG. 5 illustrates electrical activity of a beat for which no LAT is detected 410 and a beat for which LAT is detected 420. In some embodiments, the predefined condition may comprise a time of occurrence of the largest rapid deflection of the electrogram at the location, and the LAT is assumed to be the time from reference instance to the following onset of the largest rapid deflection of the electrogram of the location. In the embodiment illustrated in FIG. 5, LAT is detected at 421. LATs may be positive or negative. Methods for determining the time of occurrence of the largest rapid deflection of the electrogram, and other definitions and conditions for determining the LAT, are familiar to those skilled in the art, and all such methods, definitions, and conditions are assumed to be comprised within the scope of the present invention.

In some embodiments, if a beat has LAT, certain filters may be applied to the beat, as discussed in more detail below. In some embodiments, beats with LAT may be selected over adjacent beats without LAT.

Figure 6:
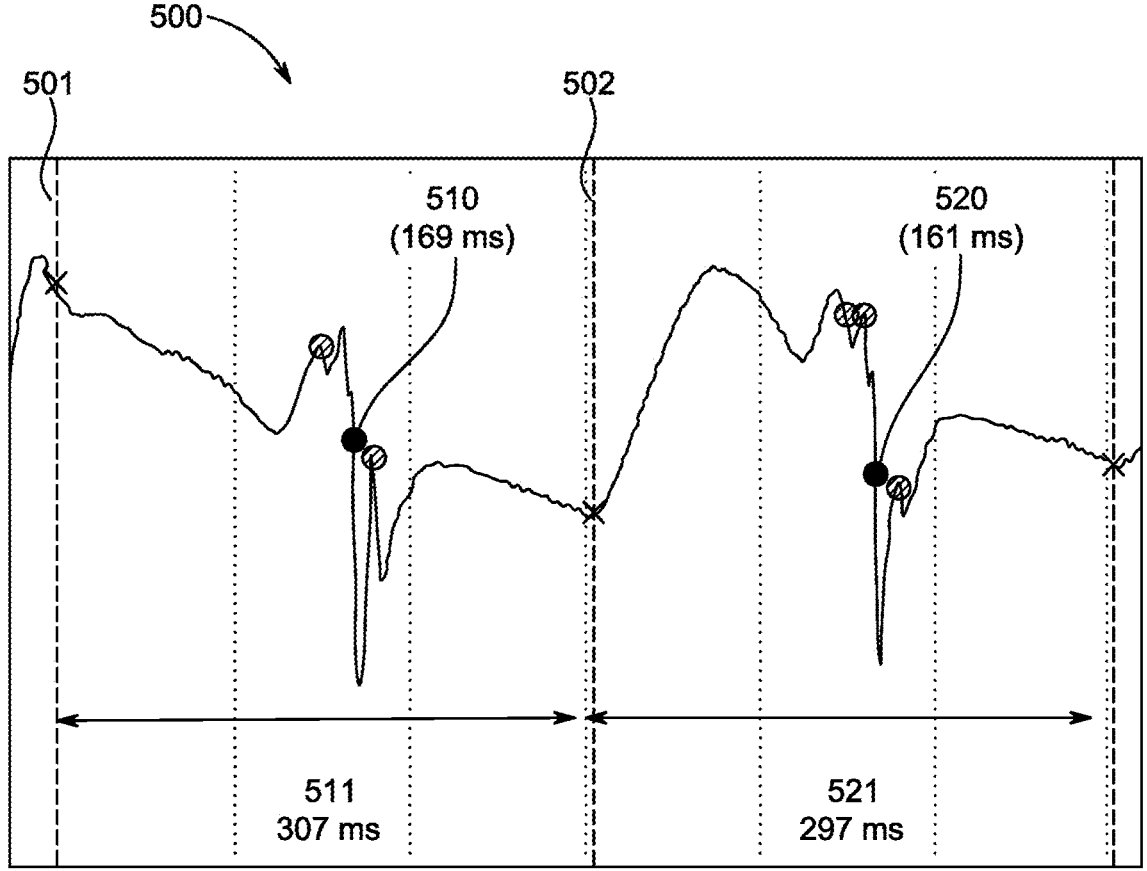
FIG. 6 is a graph of electrical activity with a beat for which LAT is detected, according to an exemplary embodiment.

The algorithm may comprise a relative LAT stability filter. In further embodiments, relative LAT stability may be used as a filter in Phase II of the algorithm. FIG. 6 is a graph 500 of local excitation versus time. The lapsed time between a start of the first cycle 501 and a first local excitation 510 is determined. In the example illustrated in FIG. 6, the first lapsed time is 169 ms. The lapsed time between a start of the second cycle 502 and a second location excitation 520 is determined. In the example illustrated in FIG. 6, the second lapsed time is 161 ms. LAT stability may be calculated using Equation 1, where $LAT_{i-1}$ is the LAT value for the first cycle and $LAT_i$ is the LAT value for the second cycle.

$$LAT_i - LAT_{i-1} = LAT \ Stability \qquad \text{Eq. 1}$$

As such, in the example illustrated in FIG. 6, if Equation 1 is used to determine the relative LAT stability, the relative LAT stability would equal 8 ms. The relative LAT stability may be compared to a threshold to filter. For example, the threshold may be 3 ms. If the threshold were 3 ms, the beat would not pass the relative LAT stability criteria and therefore would not be incorporated into the mapping.

The relative LAT stability may also be calculated using Equation 2, which takes into account cycle length (CL) variability. In Equation 2, $LAT_{i-1}$ is the LAT value for the first cycle, $CL_{i-1}$ is the length of the first cycle, where LAT is the LAT value for the second cycle, and $CL_i$ is the length of the second cycle.

$$\frac{LAT_i}{CL_i} - \frac{LAT_{i-1}}{CL_{i-1}} \qquad \text{Eq. 2}$$

As such, the relative LAT stability filter enables the selection of more stable beats, which will improve the accuracy of the mapping.

Figure 7:
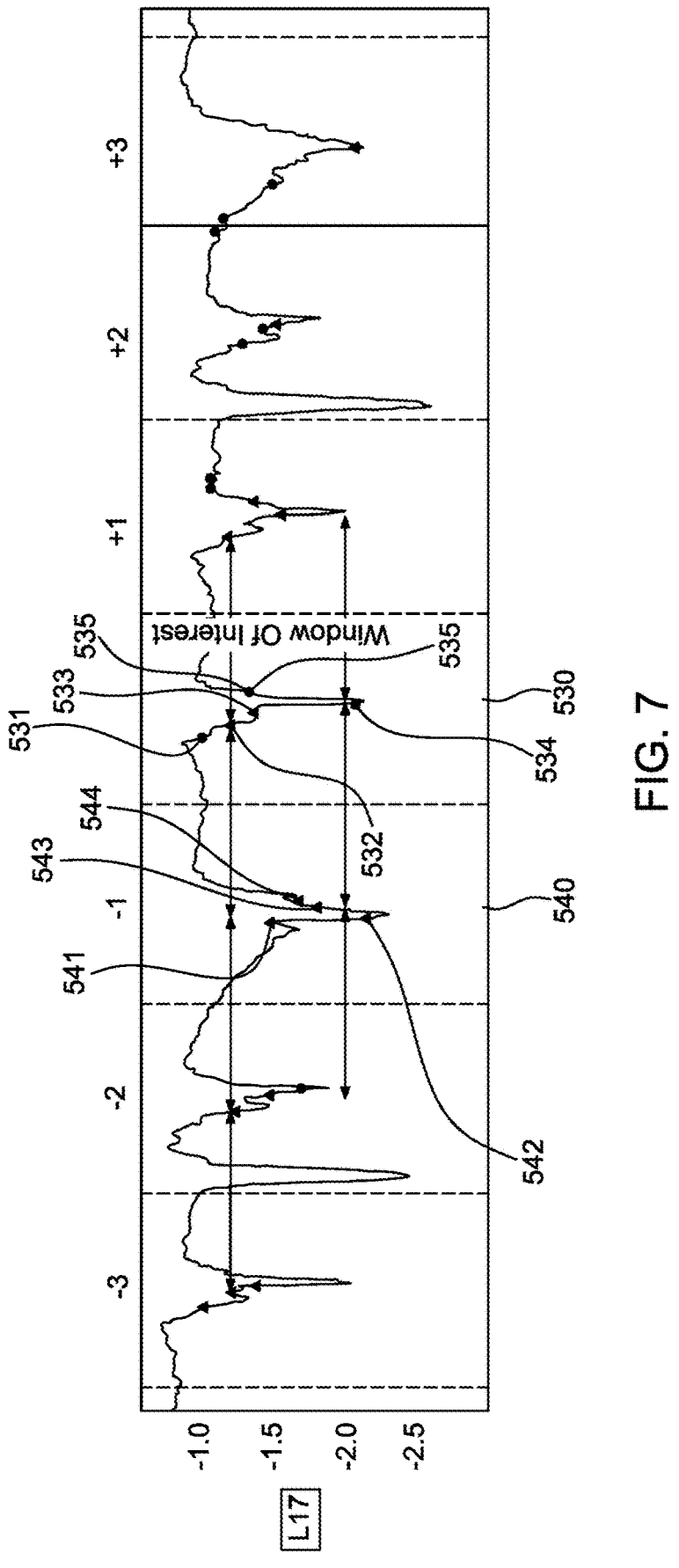
FIG. 7 is a graph of electrical activity illustrating relative LAT stability, according to an embodiment.

The relative LAT stability filter examines several beats before and after the beat of interest (BOI) 530, as shown in FIG. 7. In some embodiments, the relative LAT stability is calculated for each LAT of the BOI relative to the LATs of beats before and after the BOI. For example, in FIG. 7 the BOI 530 consists of five LATs 531-535. For each of LATs 531-535, the relative LAT stability is calculated relative to three beats before and three beats after the BOI, for a total of six calculations. In some embodiments, the relative LAT stability is calculated relative to the most stable LAT of other beats. Therefore, when calculating the relative LAT stability of LAT 531 of the BOI 530 in FIG. 7, the relative LAT stability is computed for all LATs 541-544 in beat 540, and only the most stable one is compared to each LAT of the BOI 530. In the example illustrated in FIG. 7, the most stable LAT of beat 540 is LAT 541. Therefore, each LAT 531-535 of beat 530 is compared to LAT 541 of beat 540 when calculating the relative LAT stability.

After calculating the relative LAT stability values, the relative LAT stability filter may be applied. In some embodiments, a LAT will pass the relative LAT stability filter if its relative LAT stability values relative to a certain number of beats (e.g. 2 out of the 6 beats that were examined) are below a certain threshold. The others LATs may be rejected. In some embodiments, if a beat has at least one LAT that passes the relative LAT stability filter, it is selected, otherwise it is discarded. In the example illustrated in FIG. 7, LATs 532 and 533 pass the relative LAT stability filter, and beat 530 would be selected to be integrated into the 3D mapping.

The unipolar slope of a beat may be used as a filter in the algorithm, as noted above. The unipolar slope may be measured within a defined time window. The unipolar slope may indicate whether the signal is local or far-field. In some embodiments, unipolar slopes greater than or equal to 0.03 mV/ms may indicate that the beat is local and therefore more accurate. As such, in some embodiments, only beats comprising unipolar slopes greater than or equal to 0.03 mV/ms may be considered for selection. The slope value of 0.03 mV/ms is by way of example only, and other slope thresholds may be utilized in the algorithm.

In some embodiments, the stability of a beat may be further analyzed and used. For example, such stability may be morphological (such as Pearson correlation) or simple slope measurements requiring a beat to have a similar slope at a similar LAT to another beat.

The algorithm may comprise a bipolar voltage filter, as noted above. In some embodiments, the system may utilize the Pentaray™ catheter or probe from Biosense Webster with a bipolar configuration in which a signal is measured between two adjacent electrodes on a spine, as discussed above. A higher bipolar voltage may be more desirable, as it may indicate a stronger signal. In some embodiments, beats comprising voltages greater than or equal to 0.1 mV may be considered for selection. If the voltage is relatively low (for example, less than 0.1 mV), additional filters, such as TPI, may be considered.

TPI may be a filter utilized in the algorithm, as noted above. TPI may indicate whether the catheter 14 is in proximity to tissue or not. In some embodiments, the TPI may be positive or negative and may indicate whether the catheter 14 is in proximity to tissue, not in proximity to tissue, or if it is unknown. In some embodiments, beats collected when the catheter 14 was in contact with or in proximity to tissue are preferable. In some embodiments, if the catheter 14 is touching the tissue, the beat may indicate characteristics of the tissue. For example, if the TPI indicates that the catheter 14 was in proximity to the tissue when the beat was collected and the beat is weak, it may be determined that the tissue in contact with the catheter 14 is scarred. Scarred tissue may be indicated on the 3D map by color, texture, pattern, or the like. Further, the TPI value may be recalculated using new information that is provided to system and selecting a beat that originally did not have sufficient evidence for contact. Further, TPI values may be used instead of a binary contact or no contact determination, to enable selection of beat with a high likelihood of contact.

The algorithm may comprise a fractionation stability filter, as noted above. Fractionated signals may be identified using techniques known in the art. In some embodiments, fractionated signals may be identified using methods described in commonly assigned U.S. Pat. No. 9,380,953, which is incorporated by reference as if fully set forth. In some embodiments, beats comprising fractionated signals may be of interest and therefore may be selected for integration in the 3D mapping. In further embodiments, fractionation stability may be considered for fractionated signals.

Figure 8:
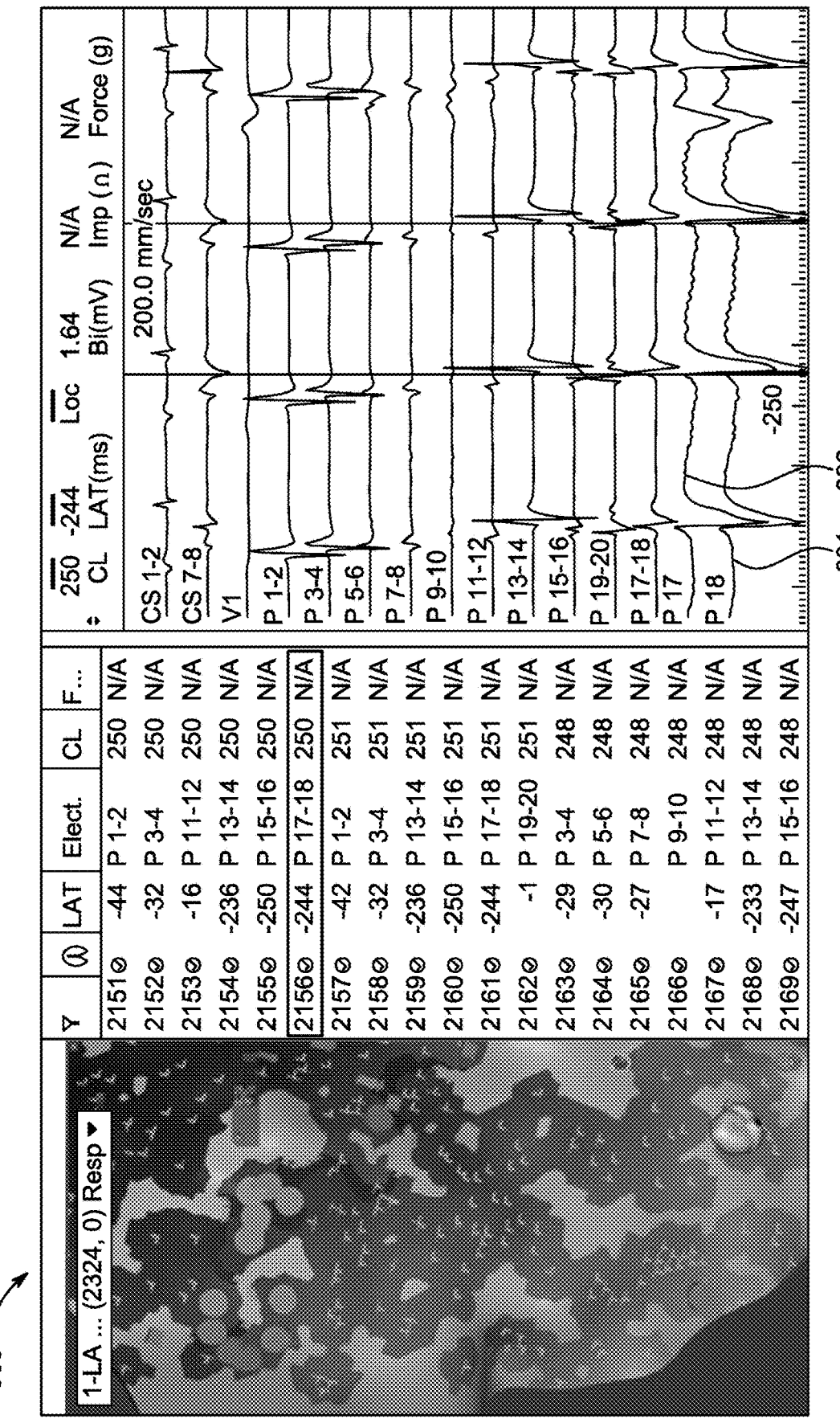
FIG. 8 is a graph of electrical activity with noise, according to an exemplary embodiment.

The algorithm may comprise a noise level filter, as noted above. In some embodiments, noise level may be monitored continuously and the noise level filter may only select beats with noise levels below a certain threshold. FIG. 8 is a graph of electrical activity 600 of a plurality of beats, including beats 601 and 602. In FIG. 8, both beat 601 and beat 602 have noise. In some embodiments, beat 601 may meet the noise threshold and beat 602 may not meet the noise threshold. In other embodiments, both beat 601 and beat 602 may not meet the noise threshold. Filtering for noise may reduce beats with far field signals. In some embodiments, the noise threshold may be applied in real-time. Additionally or alternatively, the noise threshold may be applied retro-actively.

In some embodiments, the algorithm may comprise three phases: Phase I, Phase II, and Phase III. In Phase I, one or more "common" filters may be applied to all collected beats. The common filters may include, but are not limited to: position stability, inner distance, catheter filter, cycle length, ventricle activity, respiration cycle indication, pattern matching, and/or noise. The three phases of the algorithm are provided by way of example only, and more or less phases may be utilized in the algorithm. Further, in some embodiments, a phase may be continuously executed as new data is received.

In some embodiments, after the filters in Phase I are applied, the filters that meet the criteria move to Phase II. The Phase II filters may be specific filters for specific sub-groups of beats, including, but not limited to, beats comprising no LAT, LAT and high voltage, LAT and low voltage, double potentials, and fractionated. These sub-groups, and their predefined filters, may be defined by a user. The additional filters that may be applied during Phase II may comprise one or more of the following filters: relative LAT stability, unipolar slope, bipolar voltage, TPI, and fractionation stability. Phase II may be continuously executed as new additional data is received.

During Phase III, a spatial density filter and/or a time density filter may be applied. By applying a spatial density filter, the optimal beat within a spatial area may be determined. By applying a time density filter, the optimal beat within a time range may be determined.

Figure 9:
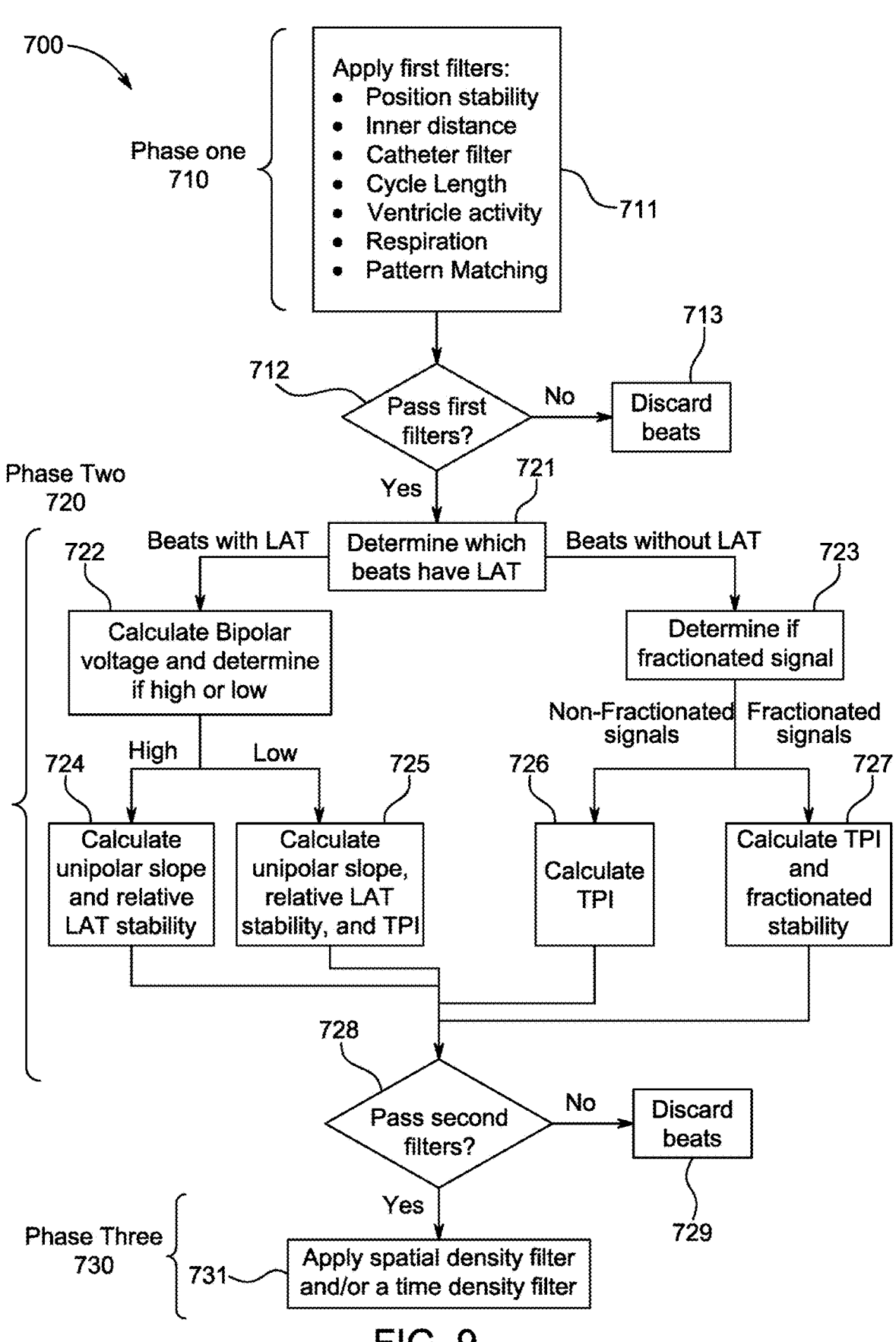
FIG. 9 is a flow chart of an algorithm for optimal beat selection, according to an exemplary embodiment.

FIG. 9 is a flow chart of an algorithm 700 for optimal beat selection for 3D anatomical reconstruction, according to an exemplary embodiment. FIG. 9 is one embodiment, and other filter combinations may be utilized. The algorithm may be used to perform the dynamic filtering 302 in FIG. 3. In the embodiment illustrated in FIG. 9, the algorithm comprises three phases: Phase I 710, Phase II 720, and Phase III 730.

During Phase I 710, one or more first filters may be applied to the collected beats at 711. In the embodiment illustrated in FIG. 7, the first filters may comprise one or more of: position stability, inner distance, catheter filter, cycle length, ventricle activity, respiration, pattern matching, and/or noise, as discussed above. Phase I 710 may not include all of the filters listed and/or may include additional filters not listed. At 712, the beats that pass the filters of Phase I 710 may pass to Phase II 720. Beats that do not pass the filters of Phase I may be discarded at 713. In some embodiments, beats may only need to meet a certain number of criteria to pass on to Phase II 720. For example, and by way of example only, beats may only need to meet five out of the eight criteria to pass on to Phase II 720. The five criteria may be any of the eight criteria listed.

In Phase II 720, one or more of the following filters may be calculated and subsequently analyzed: LAT, relative LAT stability, unipolar slope, bipolar voltage, TPI and fractionation stability. In some embodiments, beats may only need to meet a certain number of criteria in Phase II 720.

Different filters may be applied depending on characteristics of the beat. For example, in Phase II 720 the beats may be analyzed to determine if they have LAT at 721. If a beat has LAT, the bipolar voltage may be calculated and analyzed at 722. In some embodiments, the algorithm determined if the bipolar voltage is high or low. In some embodiments, a beat is considered as having a "high" bipolar voltage if the bipolar voltage is greater than or equal to 0.1 mV and "low" bipolar voltage if the bipolar voltage is less than 0.1 mV. However, as will be appreciated by one having ordinary still in the art, the bipolar voltage "high" and "low" thresholds may vary. If it is determined that a beat with LAT has a "high" bipolar voltage, the unipolar slope and relative LAT stability of the beat may be calculated and analyzed at 724. If it is determined that a beat with LAT has a "low" bipolar voltage, the unipolar slope, relative LAT stability, and TPI of the beat may be calculated and analyzed at 725.

If a beat does not have LAT, the algorithm may determine if the beat comprises a fractionated signal at 723. If the beat does not comprise a fractionated signal, the algorithm may calculate the TPI for the signal at 726. If a beat comprises a fractionated signal, the algorithm may calculate the TPI as well as fractionation stability for the beat at 727.

At 728, a plurality of second filters may be applied to beats passing the first filters. In some embodiments, the second filters that are applied to each beat is based on the characteristics of each beat. For example, the following filters may be applied to a beat determined to have LAT and high voltage to have one or more of the following characteristics: a unipolar slope of greater than or equal to 0.03 mV/ms and a relative LAT stability of 3 ms. The provided thresholds are by way of example only, and various other thresholds may be utilized in the algorithm. Further, a beat determined to have LAT and low voltage, in addition to having a unipolar slope greater than or equal to 0.03 mV/ms and a relative LAT stability of 3 ms, may also need a TPI which indicates that the beat was collected when the catheter 14 was in contact with tissue to pass the second filters.

By way of example only, a beat determined to have no LAT and to not be fractionated may need a TPI which indicates that the beat was collected when the catheter 14 was in contact with tissue to pass the second filters. A beat determined to have no LAT and to be fractionated, in addition to having a TPI indicating contact, may need a satisfactory fractionation stability to pass the second filters.

Beats that do not pass the second filters may be discarded at 729. In some embodiments, beats that pass the second filters may be selected. In other embodiments, beats that pass the second filters may proceed to Phase III 730. At 731, a spatial density filter and/or a time density filter may be applied.

Filters may be utilized so that the beat filtering and map building processes will be more dynamic to provide optimal beat selection and map building. For example, beats may be selected for the mapping, deselected for the mapping, and replaced with another beat for the mapping. There may be certain criteria for selection, deselection and replacement. For example, a beat with LAT may replace a beat without LAT in the mapping, as discussed above.

Using the above-described systems and methods, better quality and representative beats may be integrated into a 3D mapping, thereby achieving a more accurate and comprehensive mapping. The resulting mapping may be displayed on a display of the system. In some embodiments, the display is a graphical user interface (GUI). The characteristics of a beat (e.g., high bipolar voltage) may be denoted by a color, pattern, etc. in the mapping.

Figure 10A:
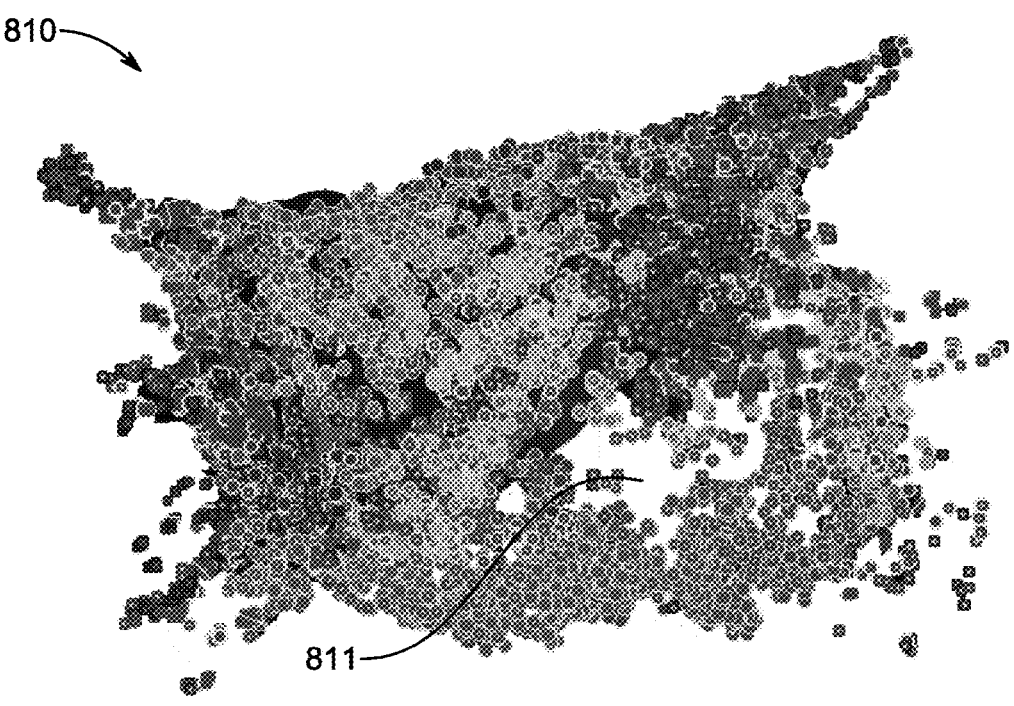
FIG. 10A is a mapping 810 generated using current implementations.
Figure 10B:
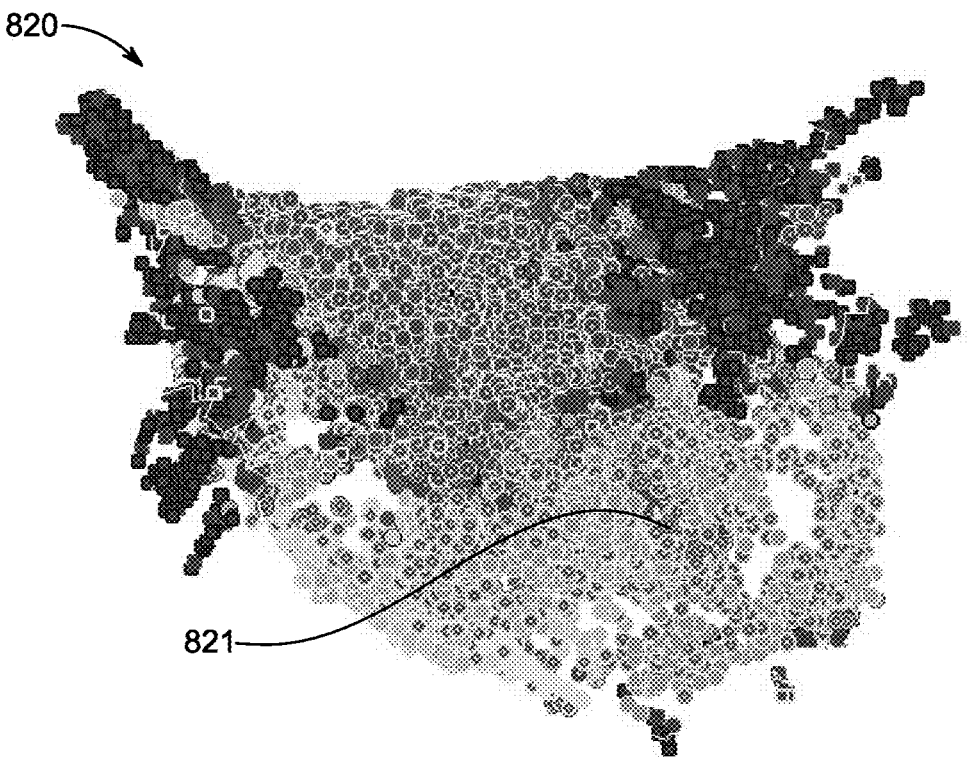
FIG. 10B is a mapping 820 generated using a method for optimal beat selection, according to an exemplary embodiment.

FIG. 10A is a mapping 810 generated using current implementations and FIG. 10B is a mapping 820 generated using the methods and systems disclosed herein. The mapping 810 generated using currently implementations is generated using about 5,000 beats. The mapping 820 generated using the methods and systems disclosed herein, on the other hand, uses about 10,000 beats. Not only are more beats selected for a more comprehensive mapping, the selected beats are better quality more and representative of the target anatomy. For example, the mapping 810 generated using current implementations has a relatively large void area 811. The mapping 820 generated using the disclosed methods and systems does not include this void, and the corresponding area 821 is able to be accurately mapped.

The methods described herein may comprise algorithms that can be utilized by a skilled software engineer to generate the requisite step-by-step computer codes for implementation of the overall method in a computer system (e.g., a general-purpose computer or a special purpose computer such as the Carto system).

Although the present disclosure relates mainly to a chamber of a heart, it is noted that the techniques described herein may also be used to model any other anatomical or non-anatomical structure. For example, the techniques described herein may be used in depth-sensing applications.

It should be understood that many variations are possible based on the disclosure herein. Although features and elements are described above in particular combinations, each feature or element can be used alone without the other features and elements or in various combinations with or without other features and elements.

What is claimed is:

1. A method comprising:
   receiving a plurality of beats from a catheter at a target mapping site;
   applying one or more first filters to each beat of the plurality of beats to determine a first subset of the plurality of beats;
   calculating one or more features of each beat of the first subset of the plurality of beats;
   applying one or more second filters to each beat of the first subset of the plurality of beats to determine a second subset of the plurality of beats, wherein the one or more second filters are associated with the calculated features;
   selecting optimal beats from the second subset of the plurality of beats; and
   integrating the optimal beats into a 3D mapping.

2. The method of claim 1, wherein the target mapping site is a chamber of a heart.

3. The method of claim 1, wherein the one or more first filters comprise one or more of: position stability, inner distance, catheter, cycle length, ventricle activity, respiration, pattern matching, and/or noise.

4. The method of claim 1, wherein the calculated one or more features comprise one or more of: local activation time (LAT), bipolar voltage, fractionation, and/or double potentials (DP) signals.

5. The method of claim 4, wherein the calculated one or more features further comprise one or more of: unipolar slope, relative LAT stability and/or slope stability, tissue proximity indicator (TPI) and value, and/or fractionation stability.

6. The method of claim 1, wherein the one or more second filters that are applied to each beat of the first subset of beats depend on the calculated one or more features of the respective beat.

7. The method of claim 1, further comprising applying one or more third filters.

8. The method of claim 7, wherein the one or more third filters comprise one or more of: a spatial density and/or a time density.

9. A system comprising:
   a processor configured to:
      receive a plurality of beats from a catheter at a target mapping site;
      apply one or more first filters to each beat of the plurality of beats to determine a first subset of the plurality of beats;
      calculate one or more features of each beat of the first subset of the plurality of beats;
      apply one or more second filters to each beat of the first subset of the plurality of beats to determine a second subset of the plurality of beats, wherein the one or more second filters are associated with the calculated features;
      select optimal beats from the second subset of the plurality of beats; and
      integrate the optimal beats into a 3D mapping.

10. The system of claim 9, further comprising a display configured to display the 3D mapping.

11. The system of claim 10, wherein the display is a graphical user interface (GUI).

12. The system of claim 9, wherein the target mapping site is a chamber of a heart.

13. The system of claim 9, wherein the one or more first filters comprise one or more of: position stability, inner distance, catheter filter, cycle length, ventricle activity, respiration, pattern matching, and/or noise.

14. The system of claim 9, wherein the calculated one or more features comprise one or more of local activation time (LAT), bipolar voltage, fractionation, and/or double potentials (DP) signals.

15. The system of claim 14, wherein the calculated one or more features further comprise one or more of unipolar slope, relative LAT stability, tissue proximity indicator (TPI), and fractionation stability.

16. The system of claim 9, wherein the one or more second filters that are applied to each beat of the first subset of beats depend on the calculated one or more features of the respective beat.

17. The system of claim 9, wherein the processor is further configured to apply one or more third filters.

18. The system of claim 17, wherein the one or more third filters comprise one or more of spatial density filter and/or time density filter.

19. A tangible non-transitory computer-readable medium in which program instructions are stored, which, when read by a processor, cause the processor to:

receive a plurality of beats from a catheter at a target mapping site;

apply one or more first filters to each beat of the plurality of beats to determine a first subset of the plurality of beats;

calculate one or more features of each beat of the first subset of the plurality of beats;

apply one or more second filters to each beat of the first subset of the plurality of beats to determine a second subset of the plurality of beats, wherein the one or more second filters are associated with the calculated features;

select optimal beats from the second subset of the plurality of beats; and integrate the optimal beats into a 3D mapping.

20. The tangible non-transitory computer-readable medium of claim 19, wherein the one or more second filters that are applied to each beat of the first subset of beats depend on the calculated one or more features of the respective beat.

* * * * *